(12) United States Patent
Thielemans et al.

(10) Patent No.: US 8,098,916 B2
(45) Date of Patent: Jan. 17, 2012

(54) SYSTEM AND METHOD FOR IMAGE-BASED ATTENUATION CORRECTION OF PET/SPECT IMAGES

(75) Inventors: Kris Flip Johan Jules Thielemans, Putney (GB); Alexander Ganin, Whitefish Bay, WI (US); Evren Asma, Niskayuna, NY (US); Ravindra Mohan Manjeshwar, Glenville, NY (US)

(73) Assignee: General Electric Company, Schenectady, NY (US)

( * ) Notice: Subject to any disclaimer, the term of this patent is extended or adjusted under 35 U.S.C. 154(b) by 799 days.

(21) Appl. No.: 12/118,170

(22) Filed: May 9, 2008

(65) Prior Publication Data

US 2009/0110256 A1    Apr. 30, 2009

Related U.S. Application Data

(60) Provisional application No. 60/983,777, filed on Oct. 30, 2007.

(51) Int. Cl.
*G06K 9/00* (2006.01)
(52) U.S. Cl. ................. 382/131; 382/154
(58) Field of Classification Search ......... 382/128–132, 382/154, 284
See application file for complete search history.

(56) References Cited

U.S. PATENT DOCUMENTS

| | | | |
|---|---|---|---|
| 2004/0260176 A1* | 12/2004 | Wollenweber et al. | 600/427 |
| 2005/0129295 A1* | 6/2005 | Shanmugam et al. | 382/131 |
| 2007/0081704 A1* | 4/2007 | Pan et al. | 382/128 |
| 2008/0219534 A1* | 9/2008 | Faul et al. | 382/131 |
| 2008/0265166 A1* | 10/2008 | Shekhar et al. | 250/363.03 |
| 2008/0273780 A1* | 11/2008 | Kohlmyer et al. | 382/131 |
| 2009/0072154 A1* | 3/2009 | Watson | 250/363.03 |
| 2010/0054571 A1* | 3/2010 | Kojima et al. | 382/131 |

OTHER PUBLICATIONS

Qi, J. and Huesman, R.J., "Propagation of Errors From the Sensitivity Image in List Mode Reconstruction", *IEEE Transactions on Medical Imaging*, vol. 23, No. 9, (2004).

Qi, J. and Huesman, R.J., "Effect of Errors in the System Matrix on Maximum a Posteriori Image Reconstruction", *Phys. Med. Biol.*, 50, 3297-3312 (2005).

Kinahan, Paul E. and Alessio, Adam M., et al., "Dual Energy CT Attenuation Correction Methods for Quantitative Assessment of Response to Cancer Therapy with PET/CT Imaging", *Technology in Cancer Research and Treatment*, vol. 5, No. 4, 319-327 (2006).

Bai, Chuanyong and Kinahan, Paul E., et al., "An Analytic Study of the Effects of Attenuation on Tumor Detection in Whole-Body PET Oncology Imaging", *J Nucl Med.*, 44:1855-1861 (2003).

* cited by examiner

*Primary Examiner* — Jingge Wu
(74) *Attorney, Agent, or Firm* — Hunton & Williams LLP

(57) ABSTRACT

A system and method for image-based correction including a receiver to acquire an image from one or more data storage systems, one or more processors to determine an attenuation mismatch estimate and calculate a correction for the image based on the attenuation mismatch estimate and the image, and an output to generate an attenuation mismatch corrected image based on the correction.

15 Claims, 10 Drawing Sheets

SYSTEM AND METHOD FOR IMAGE-BASED ATTENUATION CORRECTION OF PET/SPECT IMAGES

CROSS-REFERENCE TO RELATED APPLICATIONS

This patent application claims priority to U.S. Provisional Patent Application No. 60/983,777, filed on Oct. 30, 2007, the disclosure of which is hereby incorporated by reference herein in its entirety.

BACKGROUND

The present disclosure relates generally to imaging devices, and more particularly to a system and method for image-based attenuation correction of PET and/or SPECT images.

Hospitals and other health care providers rely extensively on imaging devices such as computed tomography (CT) scanners, magnetic resonance imaging (MRI) scanners, single photon emission computed tomography (SPECT) scanners, and positron emission tomography (PET) scanners for diagnostic purposes. These imaging devices provide high quality images of various bodily structures and functions. Each imaging device produces a different type of image based on the physics of the imaging process. For example, in a CT scanner, an x-ray source generates x-rays which propagate through the body and are detected by a detector on the other side of the body. The x-rays are attenuated to different degrees depending on what bodily structures they encounter, which results in an image showing the structural features of the body. CT scanners, however, are not particularly sensitive to biological processes and functions.

PET scanners, on the other hand, produce images which illustrate various biological processes and functions. A typical emission scan using a PET scanner starts with the injection of a solution including a tracer into the subject to be scanned. The subject may be human or animal. The tracer is a pharmaceutical compound including a radioisotope with a relatively short half-life, such as $^{18}$F-fluoro-2-deoxyglucose (FDG), which is a type of sugar that includes radioactive fluorine. The tracer has been adapted such that it is attracted to sites within the subject where specific biological or biochemical processes occur. The tracer moves to and is typically taken up in one or more organs of the subject in which these biological and biochemical processes occur. For example, when the tracer is injected, it may be metabolized by cancer cells, allowing the PET scanner to create an image illuminating the cancerous region. When the radioisotope decays, it emits a positron, which travels a short distance before annihilating with an electron. The short distance, also called the positron range, is typically of the order of 1 mm in common subjects. The annihilation produces two high energy photons propagating in substantially opposite directions. The PET scanner includes a photon detector array arranged around a scanning area, usually in a ring-shaped pattern, in which the subject or at least the part of interest of the subject is arranged. When the detector array detects two photons within a short timing window, a so-called 'coincidence' is recorded. The line connecting the two detectors that received the photons is called the line of response (LOR). The reconstruction of the image is based on the premise that the decayed radioisotope is located somewhere on the LOR. It should be appreciated that the annihilation occurs on the LOR and the decayed radioisotope is a positron range removed from the point of annihilation. The relatively short positron range may be neglected or may be compensated for in the reconstruction. Each coincidence may be recorded in a list by three entries: two entries representing the two detectors and one entry representing the time of detection. The coincidences in the list may be grouped in one or more sinograms. A sinogram is typically processed using image reconstruction algorithms to obtain volumetric medical images of the subject. Despite such benefits, PET scanners, however, do not generally provide structural details of the patient as well as other types of scanners such as CT and MRI scanners.

Recently PET-CT scanners have been introduced. A PET-CT scanner includes both a CT scanner and a PET scanner installed around a single patient bore. A PET-CT scanner creates a fused image which comprises a PET image spatially registered to a CT image. PET-CT scanners provide the advantage that the functional and biological features shown by the PET scan may be precisely located with respect to the structure illuminated by the CT scan. In a typical PET-CT scan, the patient first undergoes a CT scan, and then the patient undergoes a PET scan before exiting the scanner. After the CT and PET data have been acquired, the PET-CT scanner processes the data and generates a fused PET-CT image.

In normal practice, PET or SPECT images are reconstructed using attenuation correction. This is essential for quantification. For example, attenuation correction takes into account the fact that photons may be scattered by body parts so that these photons are not detected. Scattered photons that are detected may also need to be taken into account. This process is generally called "scatter correction."

Attenuation correction requires an estimate of the properties of the attenuation medium (e.g., density). This is typically based on an additional measurement, e.g. transmission scan or CT, or some other calculation or data. If the estimate is inaccurate, the resulting emission images will show artifacts. A common problem, for instance, is patient movement between the PET and CT scan (e.g., global movement, cardiac motion (heartbeat), respiratory motion (breathing), etc.). This may result in problems in data analysis. For example, cardiac scans may show a defect in the myocardium, which is only due to misalignment of the heart between PET and CT. Another example of misalignment error includes lung tumor quantification.

Currently, PET data may be gated for respiratory motion, obtaining different data sets for different stages in a breathing cycle (e.g., mid-inspiration, end of inspiration, mid-expiration, end of expiration, etc.) such that respiratory motion no longer influences the images. A major problem is obtaining matching attenuation correction. Some potential solutions may include: deformation of a fast CT (performed at breath-hold) to match the PET images; CINE CT with an afterwards averaging of CT slices acquired at different time-points (and hence breathing stages); CINE CT processed to obtain CT images in corresponding stages of the breathing cycle. In many cases, however, a remaining mismatch between the CT and PET may still be observed.

Current techniques to correct for errors in the attenuation estimate require re-reconstruction of the emission images. For example, a scanner console may include a semi-automatic method, incorporated into a software program (e.g., on GE™ PET/CT scanners this is part of a CardIQ™ software package) to realign cardiac CTs to the PET image after which a second reconstruction is performed.

Re-reconstruction is not always practical or possible as it requires access to the raw emission data, and fast processing hardware. Accordingly, existing systems do not guarantee reliable results in situations where such raw emission data are not readily available.

The present disclosure provides a system and method for addressing these deficiencies. As a result, techniques for efficiently and practically correcting misalignment and reconstructing accurate and reliable images in PET and/or SPECT using images rather than raw emission data is provided in the present disclosure. In one embodiment, the proposed system and method may be implemented offline. For example, a clinician reviewing the data may notice a mismatch between the attenuation and emission image. The method and system may allow for correction of this mismatch at a workstation, without access to the raw data. This makes the correction an image-based correction, which may be much easier to incorporate into the clinical workflow than existing methods. In addition, because CT to PET registration may be problematic resulting from errors in an emission image due to attenuation mismatch, it may also be advantageous for these errors to be immediately corrected to create an updated image. These updated images may be used for further improvement of registration. Thus, embodiments of the present disclosure may provide an improved registration technique for providing image-based correction of PET and/or SPECT images, after which a final reconstruction of the PET and/or SPECT images may be performed with the corrected attenuation image.

SUMMARY

Techniques for image-based correction are disclosed. In accordance with one particular exemplary embodiment, the techniques may be realized as a method and system for image-based correction including a receiver to acquire an image from one or more data storage systems, one or more processors to determine an attenuation mismatch estimate and calculate a correction for the image based on the attenuation mismatch estimate and the image, and an output to generate an attenuation mismatch corrected image based on the correction.

According to another exemplary embodiment, the techniques may be realized as a method and system for providing for image-based correction including at least one receiver to retrieve a first image and a second image from one or more data storage systems, and one or more processors to generate a first attenuation image based on the second image, register the second image to the first image, generate a second attenuation image based on the registration, and provide an attenuation mismatch estimate for image-based correction based on the first attenuation image and the second attenuation image.

According to another exemplary embodiment, the techniques may be realized as a method and system for providing for image-based correction including at least one receiver to retrieve a first image and a second image from one or more data storage systems, and one or more processors to generate a first attenuation image based on the second image, register the second image to the first image, generate a second attenuation image based on the registration, provide an attenuation mismatch estimate for image-based correction based on the first attenuation image and the second attenuation image, generate an attenuation mismatch corrected image based on the attenuation mismatch estimate, and to test the attenuation mismatch corrected image to determine whether the correction is larger than a predetermined threshold.

According to another exemplary embodiment, the techniques may be realized as a method and system for providing for image-based correction including at least one receiver to retrieve a first image and a second image from one or more data storage systems, and one or more processors to generate a first attenuation image based the second image, register the second image to the first image, generate a second attenuation image based on the registration, provide an attenuation mismatch estimate for image-based correction based on the first attenuation image and the second attenuation image, generate an attenuation mismatch corrected image based on the attenuation mismatch estimate, test the attenuation mismatch corrected image to determine whether the correction is larger than a predetermined threshold; retrieving raw image data, and reconstructing the raw image data to provide an improved correction image.

DETAILED DESCRIPTION

Figure 1:
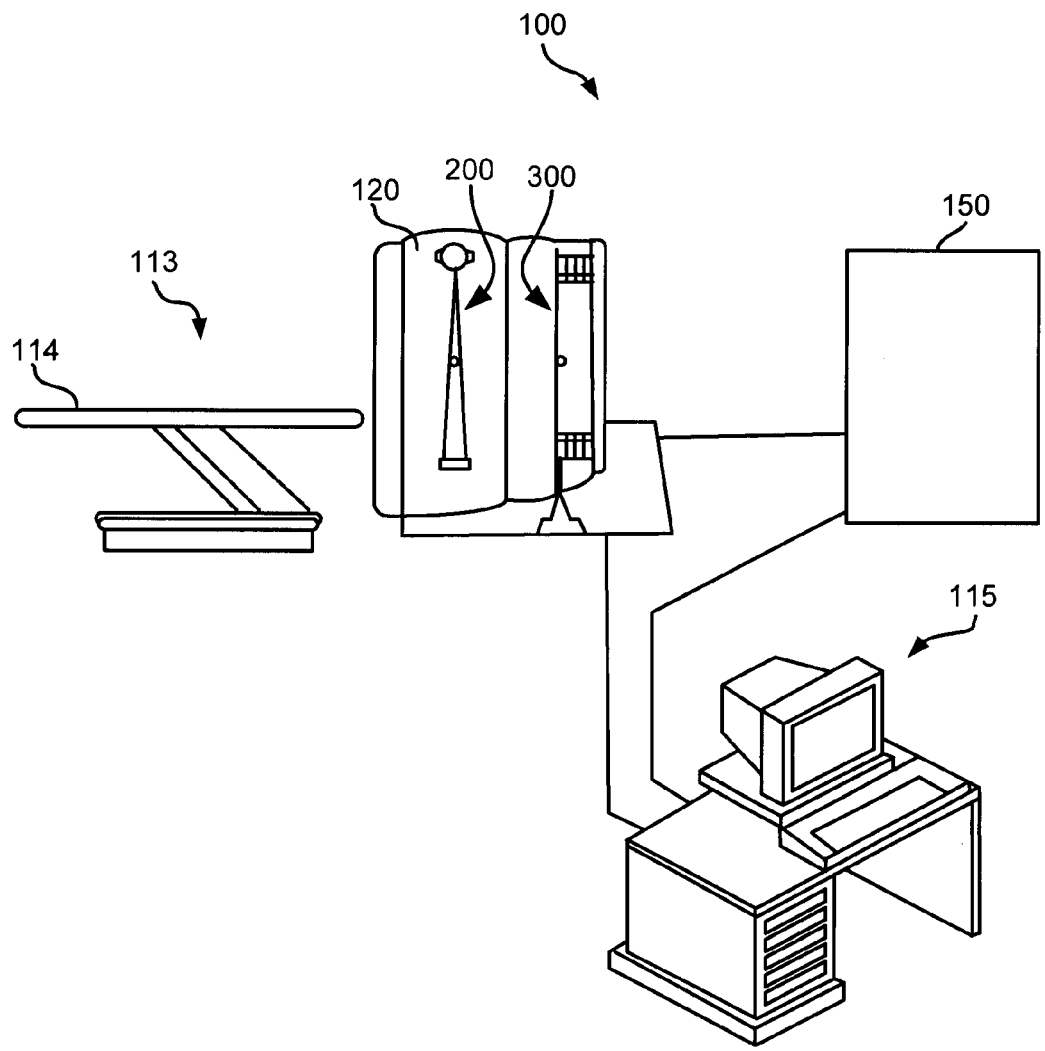
FIG. 1 depicts a PET-CT imaging system according an exemplary embodiment of the disclosure.

FIG. 1 depicts a PET-CT scanner 100 according to an exemplary embodiment of the present disclosure. The PET-CT scanner 100 may include a CT system 200 and a PET system 300 mounted around a bore in a housing 120. The PET-CT scanner 100 may also include a patient table 113, a table bed 114, a processing unit 150, and a control station 115. A patient table controller (not shown) may move the table bed 114 into the bore in response to commands received from the control station 115. The control station 115 may include a display and one or more input devices such as a keyboard, a mouse, or other similar input/controller device. Through the keyboard and associated input devices, the operator may control the operation of the PET-CT scanner 100 and the display of the resulting image on the display.

The processing unit 150 may include one or more processors, one or more memories, and other associated electronics for image processing. The processing unit 150 may process the data acquired by the CT system 200 and the PET system 300 under control of an operator operating the control station 115. Operation of the CT system 200 will be described with reference to FIG. 2. Operation of the PET system 300 will be described with reference to FIGS. 3-4.

Figure 2:
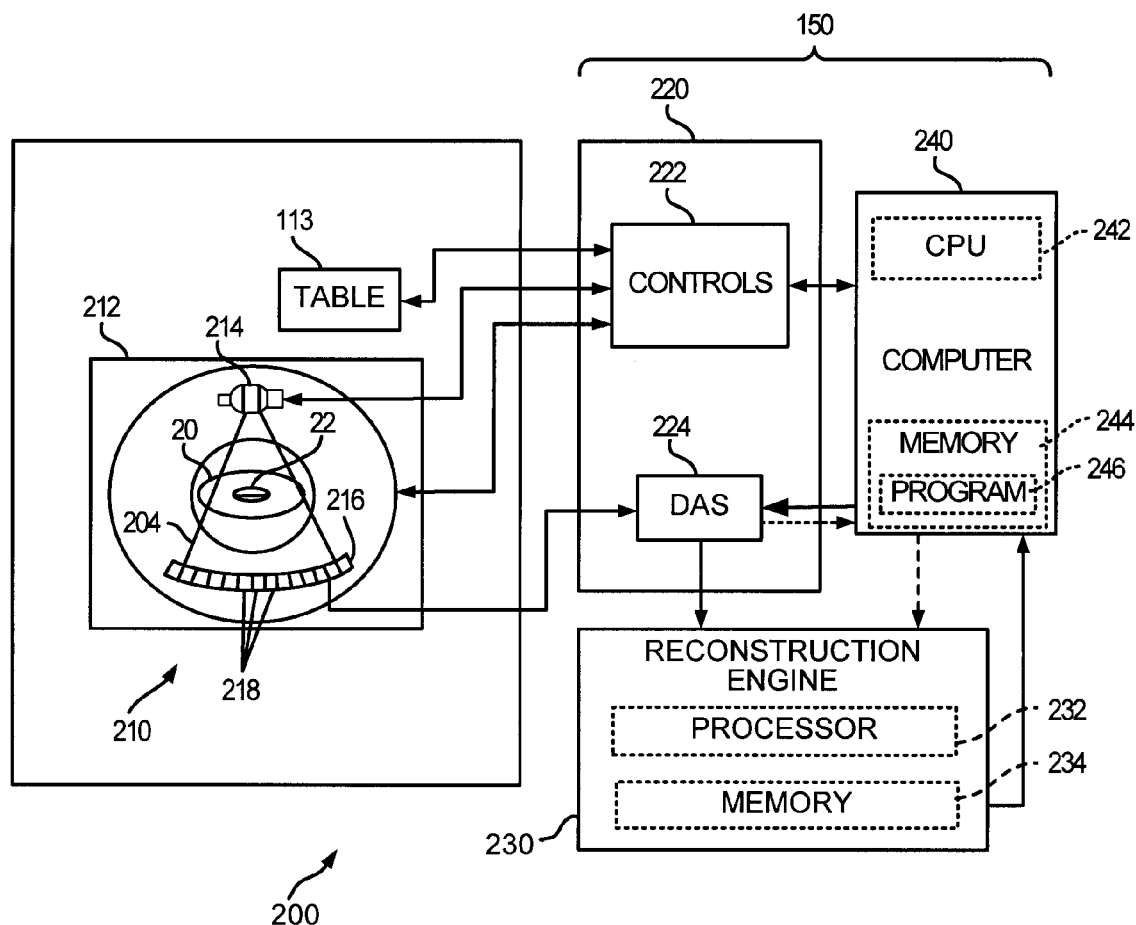
FIG. 2 depicts a CT system architecture according to an exemplary embodiment of the disclosure.

FIG. 2 depicts the major components of the CT system 200 of the PET-CT system 100 according to an exemplary embodiment of the present invention. For example, the components of the CT system 200 may be housed both in the housing 120 supporting the CT detector 200 and in the processing unit 150 shown in FIG. 1. A subject 20 for imaging may be a human patient who may be undergoing diagnostic assessment for coronary artery disease or other disease processes. X-ray tomographic imaging with such a CT system 200 may be carried out by illuminating the subject 20 with an x-ray beam 204 substantially transverse to an axis through the subject 20. The axis may generally be centered on an object 22 of interest, such as an organ or other tissue structure. The subject 20 may be located on the table bed 114 shown in FIG. 1 that translates along the direction of the axis, thereby enabling illumination of a volumetric portion of the subject 20 by the x-ray beam 204.

The CT system 200 may include a source-detector assembly, which in an exemplary embodiment may comprise a gantry 212 rotatable about the axis. An x-ray source 214, such as an x-ray tube, may be mounted on the gantry 212 and may rotate with rotation of the gantry 212. The x-ray source 214, which may comprise a collimating element (not shown), may project the beam 204 of x-rays toward a detector array 216 disposed opposite the source 214 relative to the gantry 212.

The detector array 216 may include numerous individual detector elements 218. Detector elements 218 may together provide information regarding the internal structures of the subject 20, such as the object 22. In one embodiment, each detector element 218 may generate an electrical signal indicating the intensity of a portion of the x-ray beam 204 impinging thereupon.

The signals from detector elements 218 may indicate a degree of attenuation of the beam 204 as the x-rays traverse the material or substance of the subject 20. In one embodiment, the source 214 may be rotated around the subject 20 to execute a scan operation whereby the CT system 200 acquires x-ray data. In another embodiment, the gantry 212, with source 214 attached to a side portion thereof, may rotate about the axis of the subject 20 to acquire x-ray data from numerous different illumination angles or "view angles."

The rotation operation for the source 214 may be controlled by a control/interface system 220. The control/interface system 220 may include a server computer residing in the processing unit 150 and the operator may interact with the control/interface system 220 by means of the control station 115 and/or other input devices. The control/interface system 220 may provide control for positioning of the gantry 212 relative to the subject 20, such as controlling speed of rotation about the axis and control of relative positions of the table 113 and the gantry 212. A controls section 222 may also provide control over x-ray generation (power and timing) of the source 214. The control/interface system 220 may also include a data acquisition system (DAS) 224 that samples the detector signals generated from the detector elements 218 and converts the sampled signals into digital data for further processing. Other various embodiments may also be provided.

A reconstruction engine 230, which may also be housed in the processing unit 150, may receive the sampled and digitized data (sometimes referred to as "projection data") from the DAS 224 and may perform image reconstruction to generate CT images. In one embodiment, the reconstruction engine 230 may include a separate processor 232 and/or memory 234. Various algorithms may be utilized for reconstructing a CT image from projection data comprising a plurality of projection views. Generally, the CT image may be generated in a format compatible with the DICOM (Digital Imaging and Communications in Medicine) standard. The DICOM standard specifies the network protocol by which two DICOM-compatible systems communicate.

In one embodiment, the reconstruction engine 230 may send the reconstructed CT image to, for example, a system management computer 240, which may also reside in the processing unit 150, for storage or further processing. The computer 240 may include a CPU (a processor) 242 and/or at least one memory 244.

Figure 3:
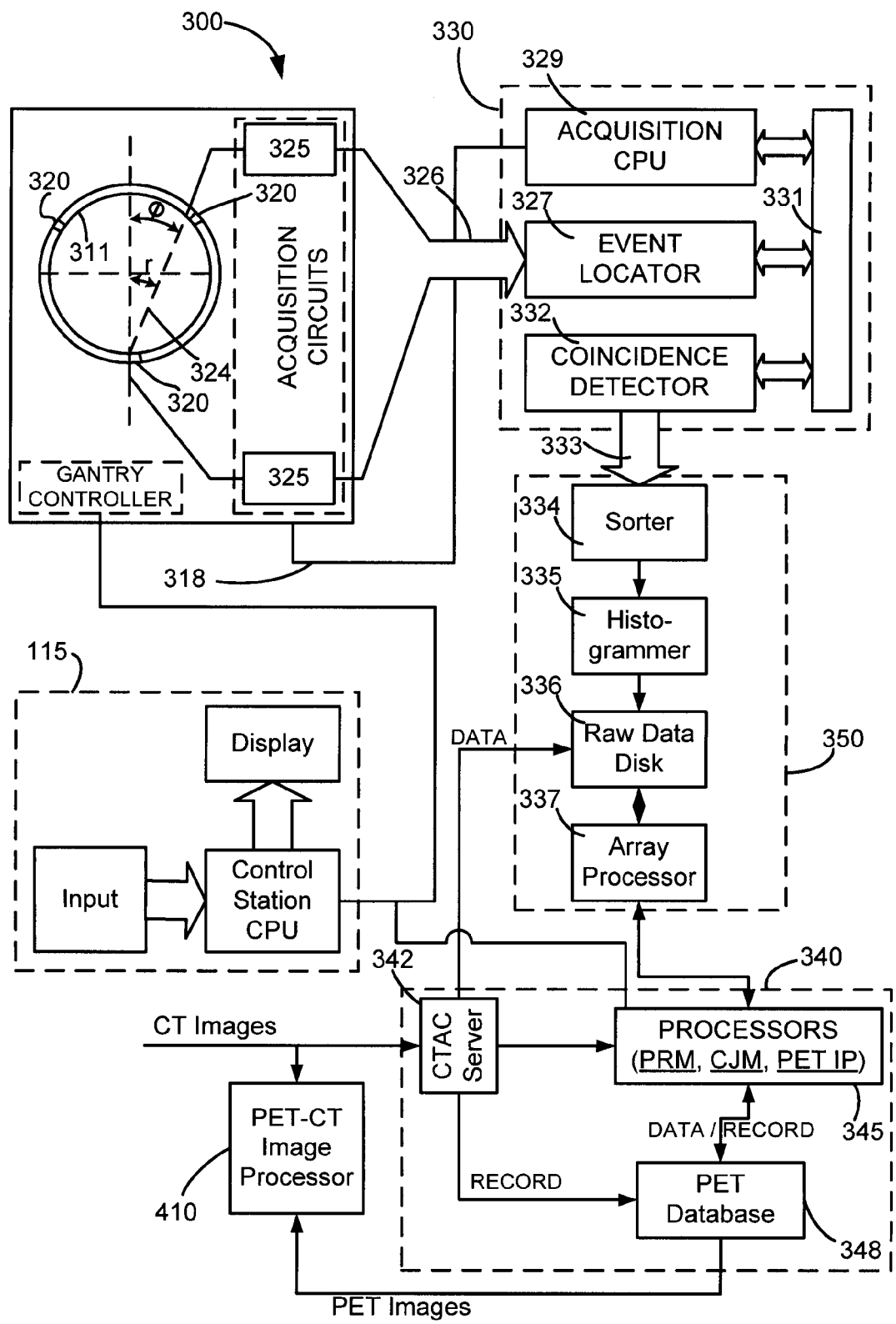
FIG. 3 depicts a PET system architecture according to an exemplary embodiment of the disclosure.

FIG. 3 depicts the major components of the PET system 300 of the PET-CT imaging system 100 according to an exemplary embodiment of the present disclosure. For example, the PET system 300 may include detector ring assembly 311 disposed about the patient bore. The detector ring assembly 311 may include multiple detector rings that are spaced along the central axis to form a cylindrical detector ring assembly. Each detector ring of the detector ring assembly 311 may be formed of detector modules 320. Each detector module 320 may include an array (e.g., a 6×6 array) of individual detector crystals which may be formed of bismuth germanate (BGO), for example. Other various detector crystals or materials may also be provided. The detector crystals may detect gamma rays emitted from the patient and in response produce photons. In one embodiment, the array of detector crystals may be positioned in front of four photomultiplier tubes (PMTs). The PMTs may produce analog signals when a scintillation event occurs at one of the detector crystals, e.g., when a gamma ray emitted from the patient is received by one of the detector crystals. A set of acquisition circuits 325 may be mounted within the housing 120 to receive these signals and produce digital signals indicating the event coordinates (e.g., the location of the detected gamma ray) and the total energy of the gamma ray. These may be sent through a cable 326 to an event locator circuit 327. In another embodiment, each acquisition circuit 325 may also produce an event detection pulse (EDP) which indicates the time the scintillation event took place.

The event locator circuits 327 may form part of a data acquisition processor 330 which periodically samples the signals produced by the acquisition circuits 325. The processor 330 may have an acquisition CPU 329, which controls communications on the local area network 318 and a backplane bus 331. The event locator circuits 327 may assemble the information regarding each valid event into a set of digital numbers that indicate precisely when the event took place and the position of the detector crystal which detected the event. This event data packet may be conveyed to a coincidence detector 332, which is also part of the data acquisition processor 330.

The coincidence detector 332 may accept the event data packets from the event locator circuits 327 and may determine whether any two of them are in coincidence. In this example, coincidence may be determined by a number of factors. First, the time markers in each event data packet may be required to be within a certain time period of each other, e.g., 12.5 nanoseconds. Second, the locations indicated by the two event data packets may be required to lie on a straight line which passes through the field of view (FOV) in the patient bore. For a detailed description of the coincidence detector 332, reference is made to U.S. Pat. No. 5,241,181 entitled "Coincidence Detector For A PET Scanner," which is hereby incorporated by reference in its entirety. Coincidence event pairs may be located and recorded as a coincidence data packet that is conveyed through a link 333 to a storage subsystem 350. In the storage subsystem 350, a sorter 334 may use a lookup table to sort the coincidence events in a 3D projection plane format. For a detailed description of the sorter 334, reference is made to U.S. Pat. No. 5,272,343 entitled "Sorter For Coincidence timing Calibration In A PET Scanner," which is hereby incorporated by reference in its entirety. The detected events may be stored in a dynamic histogram memory (histogrammer 335) where the events are ordered by radius and projection angles and other parameters. For example, in Time-of-Flight (TOF) PET scanners, the difference in arrival time of the two photons may also be recorded. In addition, the information on the energy of the photons may also be used. The PET data for a particular frame may be written to a raw data disk 336. TOF PET imaging enables time-difference measurement, e.g., determines the amount of time between the recording of one event by one of the detectors and the recording of the other event by the other detector. Therefore, if an event occurs at the midpoint between these two detectors, the difference in time would be zero. If the event occurs closer to one detector, there will be a delay before the other detector sees it. Thus, TOF makes it possible for a point of origination of annihilation to be more accurately predicted, which leads to more accurate imaging. Ultimately, improved event localization reduces noise in image data, resulting in higher image quality, shorter imaging times, and lower dose to the patient.

The PET scanner 300 may be configured to operate in two different modes, 2D and 3D, related to the annihilation events which may be observed by a particular detector ring. In one embodiment, such as in a 2D (multiplanar) mode, each detector ring is configured to only detect annihilations occurring within the plane of that respective detector ring or an immediately adjacent detector ring, and not to detect annihilations occurring at other positions within the PET scanner 300 (e.g., annihilations occurring within the other detector rings of the PET scanner). Such multiplanar data may be organized as a set of two-dimensional sinograms. In another embodiment, for example, such as in a 3D (volumetric) mode, the detectors of each detector ring may receive photons from a wider range of angles than in a 2D PET scanner.

Figure 4:
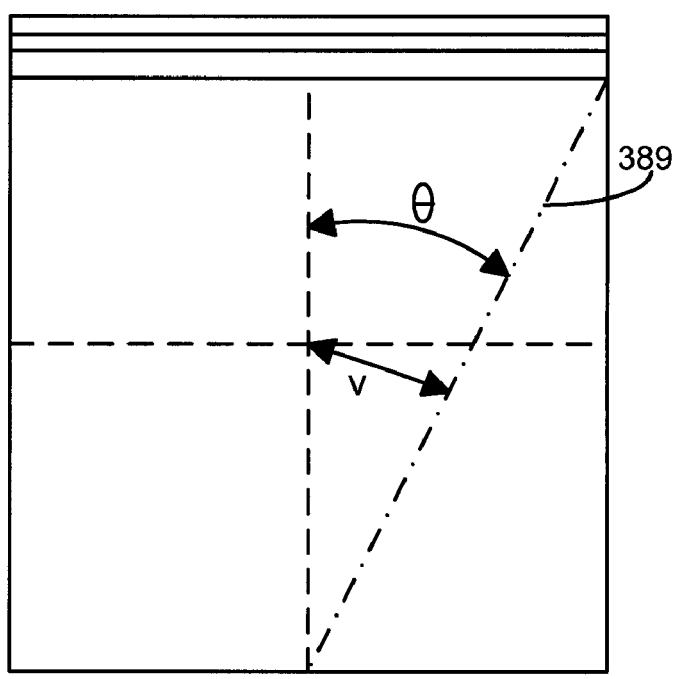
FIG. 4 depicts a illustration of variables used in the projection plane data format according to an exemplary embodiment of the disclosure.

In this example, a 3D PET scanner may determine the existence of, and process information related to, coincidence events that occur not merely between pairs of detectors positioned on a single (or immediately adjacent) detector ring, but also between pairs of detectors positioned on detector rings that are spaced more than one ring apart. Each pair of event data packets that is identified by the coincidence detector 332 may be described in a projection plane format using four variables r, v, θ and φ, e.g., according to the form $p_{\theta,\phi}(r,v)$, as shown in FIGS. 3 and 4. In particular, variables r and φ may identify a plane 324 that is parallel to the central axis of the PET scanner, with φ referring to the angular direction of the plane with respect to a reference plane and r referring to the distance of the central axis from the plane as measured perpendicular to the plane. As further shown in FIG. 4, variables v and θ may further identify a particular line 389 within that plane 324, with θ referring to the angular direction of the line within the plane, relative to a reference line within the plane, and v referring to the distance of the central point from the line as measured perpendicular to the line.

Accordingly, a 3D PET scanner may allow for increased sensitivity when compared to a 2D multiplanar scanner, since more coincidence events are recorded. However, scanning in 3D tends to admit more scattered and random coincidence events to the data set from which the image is reconstructed than scanning in 2D. As a result, since the 3D PET scanner produces more data, image processing and image reconstruction time using such data may be significantly increased.

While it should be appreciated that the PET system 300 may be configured to operate as a 2D and/or a 3D system, the PET system 300 may operate as a 3D system according to an exemplary embodiment of the present disclosure. In this example, the sorter 334 may count all events occurring along each projection ray (r, v, θ, and φ), and may store that information in the projection plane format. The PET system 300, as shown in FIG. 3, may include one or more additional processors 345 such as, for example, a prospective reconstruction manager (PRM), a compute job manager (CJM), and a PET image processor (PET IP). The processors 345 may interact with an array processor 337 in the storage subsystem 350 to process the projection plane format PET data into attenuation corrected PET images, as will be described below in more detail.

The PET system 300 may also include a computed tomography attenuation correction (CTAC) server 342. The CTAC server 342 may execute an independent process that runs in the processing unit 150. The CTAC process may receive CT image data from the CT system 200 and convert that CT image data into CTAC data. For example, the CTAC process may receive a request from the CT system and perform a bi-linear or other algorithm to convert the data from CT image units (Hu) to a PET 511 keV attenuation coefficient ($cm^{-1}$), which produces the CTAC correction for PET data from the CT images. Once the CT images are converted to CTAC data, the CTAC server 342 may write the CTAC data to the raw data disk 336 in the storage subsystem 350. At the same time, a record may be transmitted to the PET database 348 to create a data link (CTAC record) to the CTAC data.

The PET system 300 may also include a PET-CT image processor 410 which receives CT images and PET images. The CT images and the PET images may be spatially registered to each other because the patient undergoes both scans while remaining in the same position on the table bed 114. Registration may be achieved by detecting and estimating patient movement. The PET-CT image processor 410 may generate a fused PET-CT image using the input CT and PET images.

It should be appreciated that the arrangement depicted in FIGS. 1-4 is exemplary. For instance, the PET-CT scanner 100 may include different configurations or number of processors, memories, and/or other hardware, to perform various additional functions, and these components may be located at other locations such as the control station 115, or at another server or processing unit. It should also be appreciated that the PET-CT system 100 may be further configured or customized to suit various scanning needs. Other various embodiments may also be provided.

Figure 5:
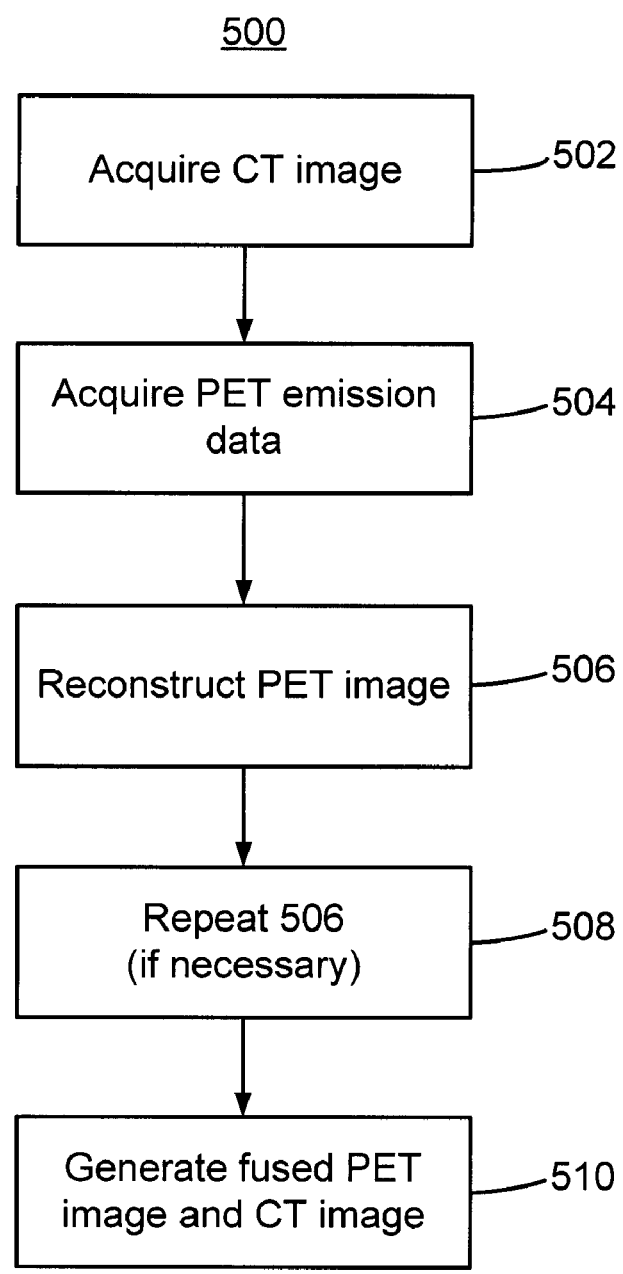
FIG. 5 depicts a diagram showing the flow of image data in a PET-CT scanner according to an exemplary embodiment of the disclosure.

Operation of the PET-CT scanner 100 will now be described according to an exemplary embodiment of the disclosure with reference to FIG. 5. FIG. 5 depicts an illustrative flowchart for acquiring of PET data and reconstruction of a PET image 500 according to an exemplary embodiment of the present disclosure. The exemplary method 500 is provided by way of example, as there are a variety of ways to carry out methods disclosed herein. The method 500 shown in FIG. 5 may be executed or otherwise performed by one or a combination of various systems. The method 500 is described below as carried out by the system 100 shown in FIG. 1 by way of example, and various elements of the system 100 are referenced in explaining the example method of FIG. 5. Each block shown in FIG. 5 represents one or more processes, methods, or subroutines carried in the exemplary method 500. A computer readable media comprising code to perform the acts of the method 500 may also be provided.

Referring to FIG. 5, the process begins at block 502, in which the CT system 200 acquires CT images. In one embodiment, the CT images may be generated from acquired CT raw data. In particular, the data acquisition system (DAS) 224 (see FIG. 2) of the CT system 200 may acquire CT data, as described above, and the reconstruction engine 230 of the CT system 200 may generate CT images for all frames prescribed by the operator of the scanner 100. At the conclusion of block 502, all of the CT images for the scan may be stored in the memory 234 of the reconstruction engine 230 or in the memory 244 of the system management computer 240. In another embodiment, the CT images may be acquired through retrieval of stored CT images (e.g., from memory 234, memory 244, etc.).

In one embodiment, the CT images, as opposed to the CT raw data, may be used for attenuation correction of the PET data during the PET image reconstruction process. Accordingly, the CT images may be transmitted to the raw data disk 336 for storage while a record is transmitted to create a data link in the PET database 348.

It should also be appreciated that the CT images may be sent to the CTAC server 342, which converts the CT images into CTAC data. Based on a bi-linear function, for example, the CT data in CT image units may be converted to PET attenuation coefficients (CTAC data). The CTAC data may be used for further attenuation correction of the PET data during the PET image reconstruction process. For example, the CTAC data may be transmitted by the CTAC server 342 to the raw data disk 336 for storage while a record is transmitted to create a data link (CTAC record) in the PET database 348. While not necessary for the various embodiments of the present invention to provide attenuation mismatch correction, the CTAC data may be used for fine tuning image reconstruction when such information is readily available.

At block 504, the PET system 300 may acquire one or more PET images. In one embodiment, a first frame of PET data may be acquired, as described above with respect to FIG. 3. The detector crystals of the PET system 300 may detect gamma rays emitted from the patient, and the acquisition circuits 325, event locator circuits 327, and coincidence detector 332 together record coincidence events which may be the basis of the PET data. The sorter 334 may use a lookup table to sort the coincidence events in a 3D projection plane format. The detected events may be stored in the histogrammer 335 where the events are ordered by radius and projection angles. At the conclusion of block 504, the PET data for a particular frame may be written to the raw data disk 336 and a data link (PET record) may be created and stored in PET database 348. In another embodiment, the PET system 300 may acquire at least an entire PET image set to be stored in at least one or more data storage systems.

According to one aspect of the disclosure, the system 100 may be programmed such that a CT prescription by the operator automatically sets up and specifies a corresponding 3D PET prescription and protocol. A PET scan data acquisition phase based on the corresponding CT scan may also be provided.

At block 506, reconstruction of the PET images may be provided. In this example, the first frame of PET data may be reconstructed into a PET image while a second frame of PET data is being acquired. In addition, the acquired PET image may be corrected based on attenuation information during CT acquisition.

At the conclusion of block 506, a PET image may be reconstructed for the current frame and may be stored in the PET database 348. In one embodiment, the reconstruction of the PET image for the current frame may occur while the PET system 300 is acquiring a PET image for the next frame. This parallel processing (PET data acquisition of next frame with PET image reconstruction of current frame) may significantly reduce the total PET-CT exam time. It should also be appreciated that PET image reconstruction may be provided in various stages or final acquisition of a PET image set as well.

At block 508, reconstructing current frame of PET image while acquiring next frame of PET data, as depicted in block 506, may be repeated, as necessary, for a plurality or all subsequent frames in the scan until all the prescribed data has been acquired and/or reconstructed.

In the event that PET reconstruction is achieved frame by frame, the PET data which have been converted to sinogram format may further be overlapped with adjacent frames. The overlap function may enhance the accuracy of the resulting PET images, e.g., by reducing or eliminating the detector sensitivity artifacts associated with 3D scans. Since one typical objective of whole-body PET scans is to produce images of uniform quality both across the imaging plane and in the axial direction (along the sections of the object imaged), overlapping may be advantageous since it reduces noise caused by lost sensitivity in the end slices. The high noise in the end slices may be reduced by weighted averaging of the low count (low-sensitivity) slices included in the overlap.

In general, the overlap process may entail defining an overlap region between two adjacent frames of PET data in terms of a number of overlapping slices. For example, a full frame of PET data may include thirty-five (35) slices, and the overlap region comprises about five (5) to seven (7) slices. Once the overlapping slices are defined, the slices may be weighted based on their proximity to the end of the frame and then may be added together. In a seven slice overlap, for example, slice twenty-nine (29) in the first frame may overlap with slice one (1) in the second frame, slice thirty (30) in the first frame may overlap with slice two (2) in the second frame, etc. The following equation may be used to calculate the weights:

weight for slice $A$=(relative position of slice $A$)/(relative position slice $A$+relative position of slice $B$)

In the above example, the relative position may be the number of slices that a particular slice is located from the end of the frame. For example, slice two (2) may have a weight of 2/8 and slice thirty (30) may have a weight of 6/8, and slice one (1) may have a weight of 1/8, and slice twenty-nine (29) may have a weight of 7/8. The weights may also be calculated with the assumption or approximation that sensitivity drops off linearly towards the detector edge. Of a pair of corresponding overlapping slices, the one which was acquired closer to the detector center may contribute more signal, and hence it may be weighted accordingly. Thus, in the event that the current frame is not the first frame, then the current frame may be overlapped with a portion of the previous frame. As a result, the overlapping slices from the previous frame may be retrieved, and the overlapping slices for the adjacent frame may be weighted, as described above, summed, and stored.

After the PET images are created, they may be transferred to the CJM 352. The CJM 352 is a server that may manage all PET reconstruction requests to the PET image processor 353 and keep track of all the jobs submitted to the processor queue, their order in the queue, and their time of completion. The CJM 352 may also send reconstruction status notifications to a user interface. The PET images may then be stored in the PET database 348.

At block 510, the CT images and the PET images may be sent to the PET-CT image processor 410 for generating a fused PET-CT image. The two image data sets (PET and CT) used to construct the fused PET-CT image may be approximately spatially registered to each other, because the patient has undergone both scans while remaining in the same position on the table bed 114. The fused PET-CT image may show anatomical structures and locations from CT along with the metabolic activity from PET. The PET-CT image processor 410 may be part of a workstation used for examining images or may be part of another part of the system 100. According to one embodiment, an eNTegra™ workstation or an Advantage™ Workstation (AW) available from GE Healthcare may be used. The eNTegra™ and AW workstations may have, among other things, an image fusion capability, which employs registration (matrix transformation) of CT's coordinate system to the PET's coordinate system.

An important ingredient of the proposed image-based correction technique is that it may also require an estimate of the error in the attenuation image that was used for the reconstruction of the emission image. For example, an estimation of error in an attenuation image due to movement and/or misalignment may be provided. According to one embodiment, given a misaligned attenuation image $\mu^{old}$ and emission image $\lambda^{old}$, (reconstructed with $\mu^{old}$), a registration process between the attenuation map and the emission image may lead to a (more) aligned attenuation image $\mu^{new}$. This registration may, for example, be image-based (using for instance mutual information registration techniques), or shape-based object alignment (this could be lesions or myocardium). The resulting aligned attenuation image may be used to estimate the error which may be expressed as:

$$\delta\mu = \mu^{old} - \mu^{new}$$

Embodiments of the present disclosure may provide a correction (approximate) of the emission image based on an estimate of the error in the attenuation image that was used for the reconstruction of the emission image, in which further reconstruction may not be necessary. Furthermore, embodiments of the present disclosure may provide an estimate of the attenuation mismatch for misalignment due to motion. In another embodiment, the method for image-based correction may be used as an intermediate block. Specifically, in the event a motion artifact is too large, re-reconstruction of the image may be provided.

Figure 6:
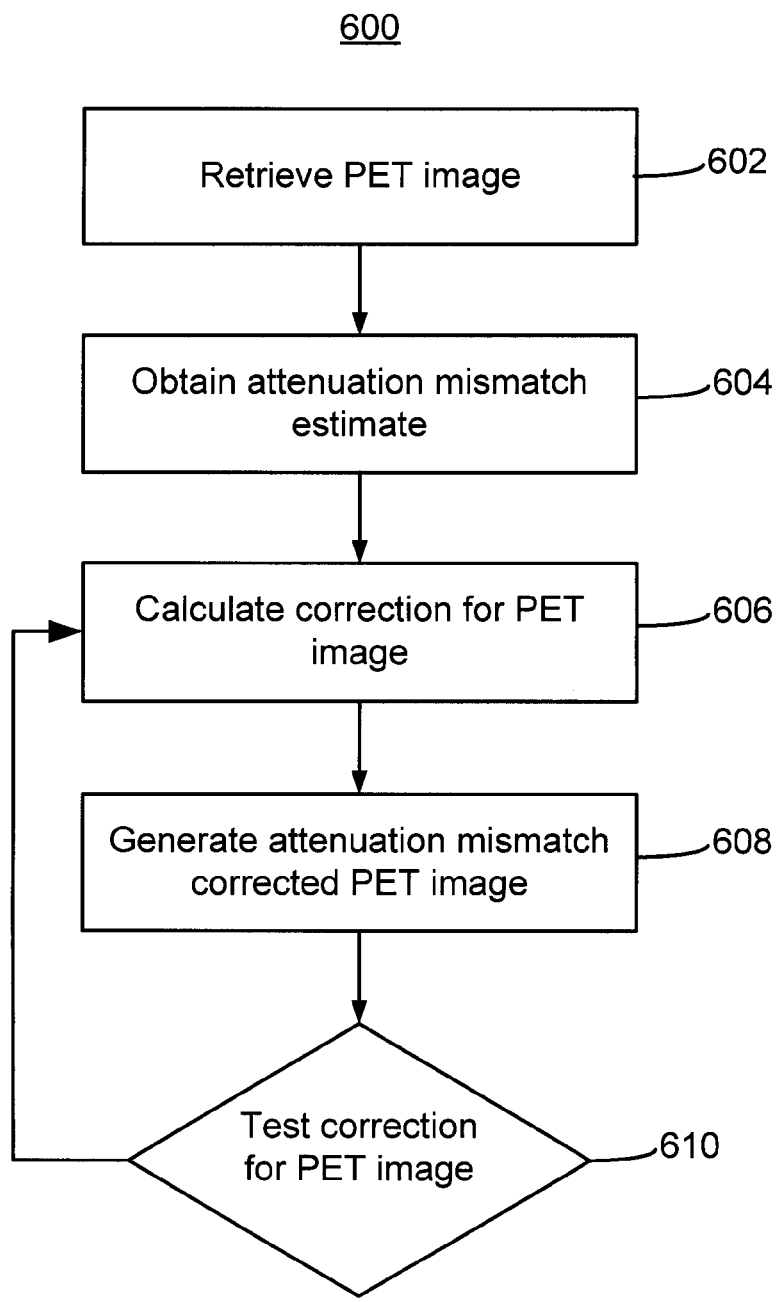
FIG. 6 depicts a flow chart showing a method of providing image-based correction according to an exemplary embodiment of the disclosure.

FIG. 6 depicts an illustrative flowchart that further details the providing image-based correction to PET images 600 according to an exemplary embodiment of the present disclosure. The exemplary method 600 is provided by way of example, as there are a variety of ways to carry out methods disclosed herein. The method 600 shown in FIG. 6 may be executed or otherwise performed by one or a combination of various systems. The method 600 is described below as carried out by the system 100 shown in FIG. 1 by way of example, and various elements of the system 100 are referenced in explaining the example method of FIG. 6. Each block shown in FIG. 6 represents one or more processes, methods, or subroutines carried in the exemplary method 600. A computer readable media comprising code to perform the acts of the method 600 may also be provided. The process of image-based correction according to an exemplary embodiment of the disclosure 600 will now be described in further detail with reference to the flowchart of FIG. 6.

Referring to FIG. 6, the exemplary method 600 may begin at block 602. At block 602, an image may be retrieved. For example, a PET or SPECT image may be retrieved from a data storage system by one or more processors at a workstation. The workstation may be local or remote to the data storage system and/or the system where the image was captured.

At block 604, an attenuation mismatch estimate may be obtained. The attenuation mismatch is generally due to errors in transmission or CTAC imaging. An approximate formula for the error in the reconstruction of emission data due to using the wrong attenuation may be derived as described below and the results applied. The current derivation may be independent of the reconstruction algorithm used to reconstruct PET images (but is therefore an approximation). In this example, a measurement model may be expressed as:

$$y = P\lambda + r$$

where P represents forward projection matrix or system matrix, $\lambda$ represents (true) emission map, r represents a background-term (e.g., to model scattered or random coincidences), and y represents a (mean of) measured data. In this equation, y and r represents vectors with length equal to the number N of bins in the histogrammed PET data and $\lambda$ is a vector with length equal to the number M of voxel elements (or in general coefficients of the basis functions) used to represent the emission distribution, and P is a M×N matrix, see for example Ollinger&Fessler, "Positron-Emission Tomography" IEEE Sig Proc Mag. (1997), 43 for more information, which is also hereby incorporated by reference in its entirety.

In this example, reconstruction with an error $\delta P$ in the forward model may result in an error $\delta\lambda$ in the image. This error may be estimated by noting that the reconstruction may attempt to find an image for which its forward projection matches the data, e.g., y−r, as expressed by Equation 1:

$$P\lambda = (P + \delta P)(\lambda + \delta\lambda) \quad \text{Equation 1}$$

Additionally, a model for the system matrix may factorize it into a geometric forward projection and a multiplicative term:

$$P = \text{diag}(n)\text{diag}(\exp(-a))G$$

$$a = G\mu$$

where G represents a geometric forward projection matrix (line integrals), $\mu$ represents an attenuation map as a vector of the same length as the emission image, a represents total attenuation on LORs, and n represents detection efficiencies, where both n and a represent vectors of the same length as y. In the above equation, the exponential may be taken on all elements of vector a, diag(n) may be a diagonal matrix with the elements of n on its diagonal and zero elsewhere, and diag(a) may also be a similar diagonal matrix.

In the event there is some error in the attenuation estimate ("attenuation mismatch"), the image may be reconstructed with an attenuation map $\mu + \delta\mu$ (and total attenuation $a + \delta a$) and the corresponding error in the reconstructed emission map may be computed using Equation 1. This may yield Equation 2, which may be expressed as (using the symbol * to denote element-wise multiplication of two vectors):

$$n*\exp(-a)*(G\lambda) = n*\exp(-a-\delta a)*(G(\lambda+\delta\lambda)) \Leftrightarrow G\delta\lambda = (\exp(\delta a)-1)*G\lambda \quad \text{Equation 2}$$

An equivalent formula may further be derived. For example, a formula to directly quantify the change in the emission image may be derived as well.

In this example, a first order approximation of this formula to be able to go to the image domain may be derived. Equation 2 may be up to first order terms equivalent to $$G\delta\lambda = (\delta a)*(G\lambda) = (G\delta\mu)*(G\lambda)$$

Supposing by way of non-limiting example that $\delta\mu$ represents tumor location mismatch and $G\lambda$ varies much more smoothly than $G\ \delta\mu$, then $G\lambda$ is approximately constant (e.g., independent of views) where $(G\ \delta\mu)$ is non-zero and may be replaced by an average value, then $$G\delta\lambda = (G\delta\mu)\text{average}(G\lambda)$$

As the average ($G\lambda$) factor is just a number (not a vector anymore), it may be brought inside the forward projection operation:

$$G\delta\lambda = G(\delta\mu\,\text{average}(G\lambda))$$

By application of a reconstruction process, this may lead to Equation 3:

$$\delta\lambda = \delta\mu\,\text{average}(G\mu) \quad \text{Equation 3}$$

Accordingly, the error in reconstructed image may be: (1) proportional to attenuation mismatch (and hence local to the region where the attenuation mismatch occurred), and (2) proportional to total activity on LORs through this region.

This derivation may hold for any reconstruction algorithm, as long as the mismatch is small and $G\lambda$ is approximately constant where $G\delta\mu$ is non-zero. However, if $G\lambda$ is not approximately constant in these elements of the sinogram, the error $\delta\lambda$ may still be roughly proportional to $\delta\mu$, but there may be other artifacts, which may depend on which reconstruction algorithm is used.

In one embodiment, $G\lambda$ may be computed by using forward projection (line integrals through the image), which is a standard operation in PET/SPECT image reconstruction. However, the assumption is that $G\lambda$ is constant for all views. Accordingly, this proportionality factor may be computed by taking the average of only a few LORs, for example by using horizontal and vertical views only, in which the forward projection procedure may be approximated by summing voxel values. Alternatively, an average summing over all LORs may provide a more accurate computation. This operation may be equivalent to back projection, which is another standard operation in image reconstruction. For example, back projection may use only the 'direct' (or '2D') LORs, which may be faster than using all possible LORs, and ultimately provides a simple way to compute the proportionality factor. In this example, the alternative formula (Equation 4) may be derived and expressed as:

$$\delta\lambda = \delta\mu^{*}(G'G\lambda)/N_{v} \quad \text{Equation 4}$$

where $G'$ represents back projection operation (which may be performed by multiplying with transpose matrix of $G$) and $N_v$ represents the number of azimuthal angles used in the (2D) forward and back projection operations. One advantage of the above formula is that it may no longer be required to compute the average of $G\lambda$ over the bins where $G\delta\mu$ is non-zero. For example, the formula may allow computation of the proportionality factors for every voxel in the image and may therefore be applicable when the error $\delta\mu$ in the attenuation map is not only non-zero in a small region such as a tumor.

It should also be appreciated that in order to apply Equations 3 and 4, a strict correspondence between the detector LORs and the LORs used to compute the average projection (by forward and back projection) may not be required. This is because the projections may vary slowly and their average may not depend strongly on which LORs are used to compute the average. Therefore, the LORs may be chosen to make the computation as efficient as possible. For example, using equidistant azimuthal angles and distance from the origin may be provided. Also, a final optimization may also be performed by noting that the forward-and-back project operation $G'G$ may correspond (in 2D) to a convolution with a $1/r$ filter. In one embodiment, this optimization may be performed by fast Fourier transforms. As a result, a sinogram format may not be required.

In the examples discussed above, Equations 3 and 4 may be derived by using first order Taylor approximations. This means that these examples may be limited to cases where the attenuation mismatch may be small or minor. Improved accuracy of the approximation may also be provided by keeping the exponential nature of the attenuation correction similar to that of Equation 2. However, according to Equation 2, doing higher order expansion in $\delta a$ may give a quadratic (or higher power) term in $G\delta\mu$, which would mean that the reconstruction of Equation 3 may no longer hold. As a result, to circumvent this issue, $\delta a$ may be replaced with its average in all higher order terms. For example, if $da=\text{average}(\delta a)$, then Equation 2 may yield Equation 5, as expressed by the following.

$$\begin{aligned}\delta\lambda &= \delta\mu * \text{average}(G\lambda)(1 + da/2 + \dots) & \text{Equation 5}\\ &= \delta\mu * \text{average}(G\lambda)(1 + (\exp(da) - 1 - da))/da)\\ &= \delta\mu * \text{average}(G\lambda)(\exp(da) - 1)/da\end{aligned}$$

Equation 5 may be similar to Equation 3, but Equation 5 may further provide a correction factor that takes the exponential behavior into account. Simulations show that this may allow the attenuation mismatch term to be much larger while still giving a good estimate of the error in the reconstructed emission image.

In this example, average($\delta a$) may be computed in several ways as discussed for $G\lambda$. In one embodiment, average($\delta a$) may be computed by the back projection argument, as expressed in Equation 6:

$$\text{average}(\delta a) = (G'G\delta\mu)/N_v \quad \text{Equation 6}$$

The derivations as described above may be compared with simulation results 700A, as depicted in FIG. 7. For example, FIG. 7 depicts results 700A from FBP and OSEM reconstruction of a uniform cylinder (20 cm diameter) in the center of the scanner 300, where the attenuation mismatch consisted of two (2) cylinders of radius 3 cm, the first cylinder with $\delta\mu = 0.04$ cm$^{-1}$ located in the center, the second cylinder with $\delta\mu = 0.03$ cm$^{-1}$ at x=90 mm. Specifically, results of reconstructions with attenuation mismatch 702, images corrected by subtracting the estimate of $\delta\lambda$ 704, and horizontal profiles through these images 706 are depicted. It should be appreciated that the corrected profiles may be flat over the region of the emission cylinder, which indicate that most of the effect of the overall attenuation mismatch may be corrected. However, minor edge effects may still be present due to resolution mismatch between the reconstruction and the estimated correction. Equations 4 and 5, for example, may compute the correction term $\delta\lambda$ at the same resolution as the attenuation mismatch estimate $\delta\mu$, while the reconstructed PET (or SPECT) image may have a different resolution, which may be due to detector size effects or post-filtering applied to the reconstructed image. Furthermore, in one embodiment, for example, $\delta\mu$ may be computed from one or more CT images (e.g., with a resolution of about 1 mm) while the reconstructed PET (or SPECT) image may have a resolution of about 8 mm. In another embodiment, this difference in resolution may be overcome by applying one or more suitable filters to the correction term. The filter may be derived from the estimated resolution of the images (e.g., by deconvolution of their respective Point Spread Functions). Alternatively, in yet another embodiment, the filter may be derived by minimizing edge effects. Accordingly, the result may illustrate that the approximations (e.g., Equations 1-6) may hold to a reasonable level for at least this application.

It should also be appreciated that image-based correction for SPECT images may also be provided. Approximations and formulas may be varied and/or tailored for providing image-based corrections for SPECT images.

For instance, in SPECT attenuation correction, reconstruction with error δP may be provided in a forward model. For example, error δλ in image may be found. The reconstruction may then attempt to find an image for which its forward projection matches the data. Referring to Equation 1:

$$P\lambda = (P+\delta P)(\lambda+\delta\lambda) \quad \text{Equation 1}$$

where the matrices are as follows $$P_{bv} = n_b G_{bv} \exp(-a_{bv})$$

$$a_{bv} = \Sigma_{b>=v'>=v} G_{bv'} \mu_{v'}$$

with v an index that may run over all image elements ("voxels") and b an index that may run over all bins in the sinogram (e.g., corresponding to detector elements in a certain position of the scanner, henceforth simply called "detectors"), such that G represents a geometric forward projection matrix (line integrals), μ represents an attenuation map as a vector of the same length as the emission image, a represents total attenuation on LORs (e.g., between voxel v and detector), and n represents detection efficiencies, where both n and a represent vectors of the same length as y.

The notation for the sum may indicate that it sums over all voxels v' between the detector b and the voxel v. It should be appreciated that the voxel-dependence of the attenuation factor may be a (conceptual) difference between SPECT and PET.

In one embodiment, when there is an attenuation mismatch, the image may be reconstructed with an attenuation map μ+δμ, and hence a+δa, where obviously $$\delta a_{bv} = \Sigma_{b>=v'>=v} G_{bv'} \delta\mu_{v'}$$

In this example, a corresponding error in the reconstructed image may be computed using Equation 1 to yield Equation 7:

$$n_b \Sigma_v \exp(-a_{bv}) G_{bv} \lambda_v = n_b \Sigma_v \exp(-a_{bv}-\delta a_{bv}) G_{bv}(\lambda_v+\delta\lambda_v)$$
$$\Leftrightarrow \Sigma_v \exp(-a_{bv}) G_{bv}(1-\exp(-\delta a_{bv}))\lambda_v = \Sigma_v \exp(-a_{bv}) G_{bv}\exp(-\delta a_{bv})\delta\lambda_v \quad \text{Equation 7}$$

It should be appreciated that Equation 7 (and all remaining equations described below) may apply for all detectors b. It should also be appreciated that these may apply to PET as well as long as $a_{bv}$ is taken independently of v.

Suppose that δμ is everywhere zero except in a small region concentrated around voxel v0, δλ may be expected to be non-zero in a region around where δμ is non-zero. As a result, $a_{bv}$ and $\delta a_{bv}$ factors in the right-hand side may be approximated by their value $a_{bv0}$ and $\delta a_{bv0}$ at that voxel, and their exponentials may be moved out of the sum in the rhs and moved to the lhs, as shown in Equation 8:

$$\exp(\delta a_{bv0})\Sigma_v \exp(a_{bv0}-a_{bv})G_{bv}(1-\exp(-\delta a_{bv}))\lambda_v = \Sigma_v G_{bv}\delta\lambda_v \quad \text{Equation 8}$$

Figure 7A:
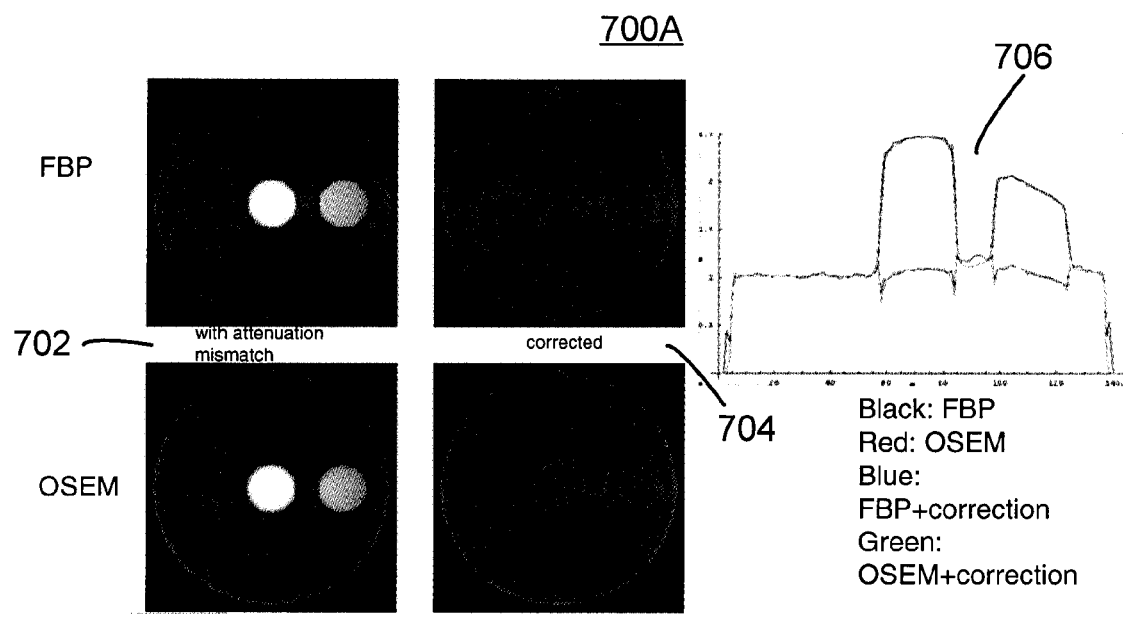
FIG. 7A depicts a screenshot of results from image-based correction according to an exemplary embodiment of the disclosure.
Figure 7B:
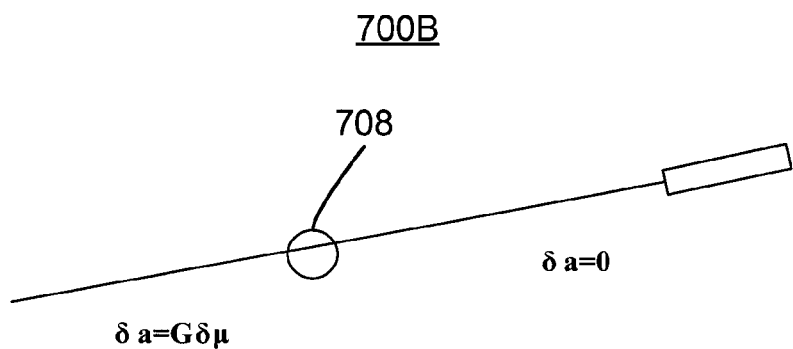
FIG. 7B depicts a screenshot of a line between a voxel and detector for image-based correction according to an exemplary embodiment of the disclosure.

However, as depicted in screenshot 700B of FIG. 7B, because δμ is everywhere zero except around v0, $\delta a_{bv}$ may be 0 for all voxels, except when the line between voxel v and detector b goes through the region around voxel v0 708, where it may be equal to $\delta a_{bv0}$, e.g., independent on v.

Using this approximation, Equation 8 may become Equation 9:

$$(\exp(\delta a_{bv0})-1)\Sigma_{b>=v0>=v}\exp(a_{bv0}-a_{bv})G_{bv}\lambda_v = \Sigma_v G_{bv}\delta\lambda_v \quad \text{Equation 9}$$

where the sum in the lhs may go over voxels v further from the detector than the tumor at v0. This equation holds for all bins b.

Similar to the PET scenario, the forward projection term in the lhs that involves the emission image may smoothly depend on the bin index b, while the forward projections of δμ ($\delta a_{bv0}$) and δλ may be non-zero in a very small part of the sinogram. Accordingly, the sum in lhs of Equation 9 may be replaced by a constant (e.g., which may be v0-dependent) obtained by averaging over bins $$\gamma_{v0} = \text{average}_b(\Sigma_{b>v0>=v}\exp(a_{bv0}-a_{bv})G_{bv}\lambda_v)$$

to obtain Equation 10:

$$(\exp(\delta a_{bv0})-1)\gamma_{v0} = \Sigma_v G_{bv}\delta\lambda_v \quad \text{Equation 10}$$

However, Equation 10 may allow calculation of δλ without reconstruction. Therefore, in order to calculate δλ, a first order approximation of this formula ($\exp(-\delta a_{bv}) \approx 1 - \delta a_{bv}$) may be derived, which may give a similar type of result as in the PET case, as shown in Equation 11:

$$(G\delta\mu)_b \gamma_{v0} = (G\delta\lambda)_b \quad \text{Equation 11}$$

where $\delta a_{bv0} = (G\delta\mu)_b$ may be used, e.g., the (geometric) forward projection of the attenuation mismatch. Since Equation 11 may be valid for all b, it may be "reconstructed" to yield Equation 12:

$$\delta\lambda_{v0} = \delta\mu_{v0} \gamma_{v0} \quad \text{Equation 12}$$

Accordingly, a local image-based correction factor may be generated, which may depend on an average forward projection of the emission image. Alternatively, in another embodiment, if the attenuation mismatch is non-zero in other voxels, the correction may be computed for more voxels in the image as shown in Equation 13:

$$\delta\lambda_v = \delta\mu_v \gamma_v \quad \text{Equation 13}$$

Similar to the PET case, higher order approximations may also be calculated in SPECT. For example, we may capture higher order terms by using an average over bins b:

$$(\exp(\delta a_{bv0})-1) = \delta a_{bv0} * ((\exp(\delta a_{bv0})-1)/\delta a_{bv0})$$
$$\sim \delta a_{bv0} \beta_{v0}, \text{ where}$$

$$\beta_{v0} = \text{average}_b((\exp(\delta a_{bv0})-1)\delta a_{bv0})$$

The constant $\beta_{v0}$ may be computed as an average after exponentiation as indicated above, or before exponentiation (e.g., using $(\exp(\delta a_{v0})-1)/\delta a_{v0}$) with $\delta a_{v0}$ an average over bins of $\delta a_{bv0}$). It should be appreciated that $\beta_{v0}$ may be equal to 1 up to first order in δμ. Thus, a minor modification of Equation 13 may yield Equation 14:

$$\delta\lambda_v = \delta\mu_{v0}\alpha_v\beta_v \quad \text{Equation 14}$$

It should be appreciated that one of ordinary skill in the art would recognize that the above derivations may be also be extended to other various embodiments, such as TOF PET. For example, in TOF, the attenuation factors may only depend on the LOR and not on the difference between the arrival times of the photons. Therefore, Equations 3 through 6 may continue to hold, where the G matrix still computes line integrals through the object. In addition, while the above derivation is independent of the reconstruction algorithm used, formulas specific to a reconstruction algorithm may be derived. For example, J. Qi and R. J. Huesman, Phys. Med. Biol. 50 (2005) 3297-3312, which is hereby incorporated by reference in its entirety, describes the effect of errors in the system matrix on maximum a posteriori image reconstruction. This particular type of reconstruction algorithm uses prior information about the image as extra input. A similar process may be applied to the embodiments of the present disclosure of attenuation mismatch to give rise to formulas and/or approximations with explicit terms taken into account.

In light of the results depicted in FIG. 7A-7B, the formulas that estimate error in the PET or SPECT emission image may then be used to correct the reconstructed emission image at one or more various components of the system 100 (e.g., the PET-CT image processor 410) in the event the attenuation mismatch δμ is known. The image dependent term may in some cases be computed using the correct emission image. However, these line integrals may not be very sensitive to attenuation mismatch, so a current estimate of the emission image may be used instead. For example, if δμ is known, δλ may be calculated, and a new image estimate may be provided as:

$$\lambda^{new} = \lambda^{old} - \delta\lambda.$$

In this example, it should be appreciated that this new image estimate may be iterated to recompute the emission dependent term (e.g., average(Gλ) in Equation 5) with greater accuracy. However, because the image-based correction may depend only weakly on the adjustments made to the emission dependent terms, it may be sufficient to apply the image-based correction only in a region of interest. Similarly, the image-based correction for a region of interest may depend only weakly on the attenuation mismatch outside this region (e.g., because of the weak dependence of the exponential terms in Equation 5). Therefore, it should also be appreciated that the combination of these two observations means that the image-based correction may need only a local estimate of the attenuation mismatch, e.g., in the neighborhood of the region of interest.

It should also be appreciated that the correction term may be proportional to δμ. In this case, the correction of the emission image may be computed where δμ is non-zero.

These observations may be particularly advantageous for the application of tumor misalignment, as the tumor (and the region of its misalignment) tends to be much smaller than the whole image.

In summary, whenever the image is reconstructed with a certain attenuation image, but a better estimate of the actual attenuation image may be found afterwards, δμ may be computed as the difference between these two, and Equation 5 may be used to correct the reconstructed PET emission image without re-reconstruction.

Referring back to FIG. 6, at block 606, a correction may be determined or calculated for the retrieved PET image. At block 608, an attenuation mismatch corrected PET image may then be generated based on the calculated correction. In one embodiment, as depicted in block 610, the correction for the PET image may be tested. For example, a test to check whether the correction is larger than a predetermined threshold may be provided. Thus, the method 600 may again re-calculate a correction for the PET image at block 606.

The predetermined threshold may be governed by various factors, including time, accuracy, or other customizable settings. In an automatic image-correction system, for example, the predetermined threshold may be set for a certain amount of time. Accordingly, testing the correction for the PET image may be looped for calculation and recalculation based on the amount of time set. In another embodiment, for example, the predetermined threshold may be set for a particular accuracy level or deviation from the previous estimate for the emission image (e.g., 1%). As a result, the loop for calculation and recalculation may end once that particular accuracy level or deviation is achieved. Block 604 may further involve an alignment step. In one embodiment, for example, the predetermined threshold may be set to a change in the alignment. In the context of a semi-automatic image-correction system, a user (e.g., clinician) may instruct the system as to whether another loop is necessary. Other various embodiments may also be provided.

Figure 8:
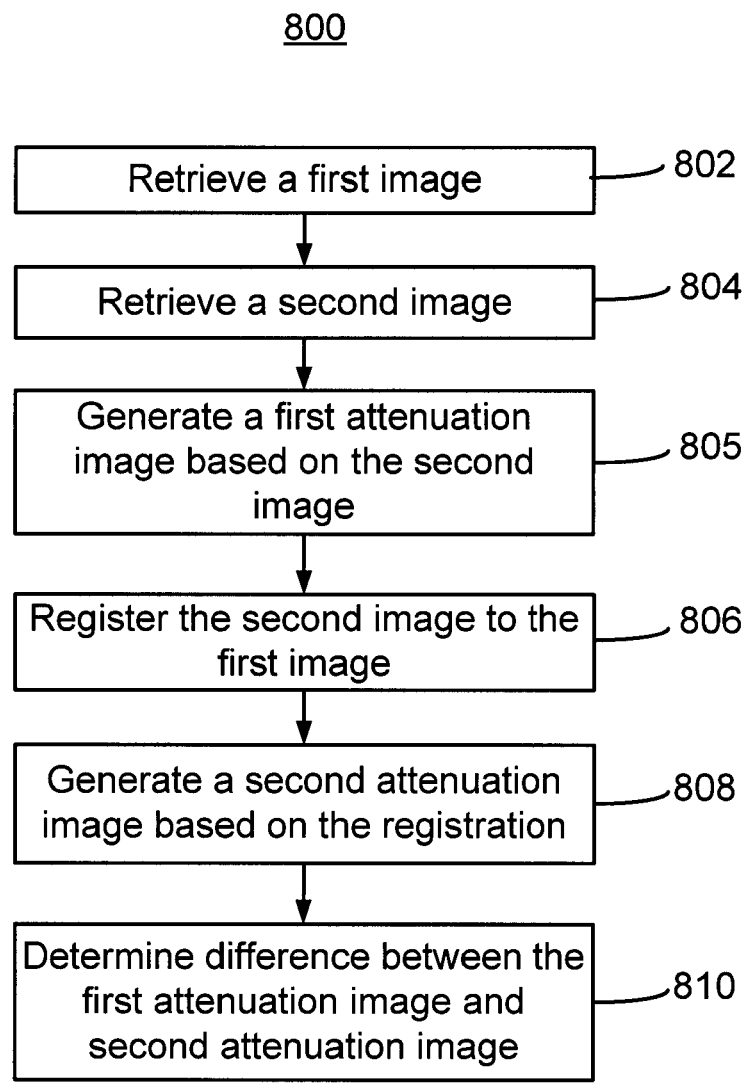
FIG. 8 depicts a flow chart showing a method of providing image-based correction according to an exemplary embodiment of the disclosure.

FIG. 8 depicts a flow chart showing a method of providing an estimate of the attenuation mismatch 800 according to an exemplary embodiment of the disclosure. The exemplary method 800 is provided by way of example, as there are a variety of ways to carry out methods disclosed herein. The method 800 shown in FIG. 8 may be executed or otherwise performed by one or a combination of various systems. The method 800 is described below as carried out by the system 100 shown in FIG. 1 by way of example, and various elements of the system 100 are referenced in explaining the example method of FIG. 8. Each block shown in FIG. 8 represents one or more processes, methods, or subroutines carried in the exemplary method 800. A computer readable media comprising code to perform the acts of the method 800 may also be provided. Referring to FIG. 8, the exemplary method 800 may begin at block 802.

At block 802, a first image may be retrieved. The first image may be a non-attenuation corrected PET or SPECT image. At block 804, a second image may be retrieved. The second image may be an image used for attenuation correction, such as CT image, an MRI, or other similar image used for attenuation correction. At block 805, a first attenuation image based on the second image may be generated. At block 806, the second image may be registered to the first.

At block 808, a second attenuation image may be generated based on the second image. In this block, δμ may be converted into correct units. In the event CT images are used as the second image (e.g., images used for attenuation correction), in one embodiment, the images may be converted to CTACs before computing the difference. Similarly, in the event MRI images are used as the images for attenuation correction, these images may undergo a similar process as well as other some more complicated conversion processes involving, for example, segmentation, atlas-mapping, etc. (see, e.g., Elena Rota Kops, Peng Qin, Mattea Müller-Veggian and Hans Herzog "MRI Based Attenuation Correction for Brain PET Images" in Advances in Medical Engineering, Springer proceedings in physics, Volume 114, which is hereby incorporated by reference in its entirety). In another embodiment, in the event PET transmission images are used as the second image, these images may already be in correct units, thereby rendering block 808 as unnecessary.

At block 810, the difference between the first attenuation image and the second attenuation image may be determined. It should also be appreciated that interpolation of the difference in these images may be provided so that the same dimensions of the images (e.g., image size, voxel size, etc.) may be provided. As a result, an attenuation mismatch estimate may be obtained.

Even though in this embodiment, a non-attenuation corrected PET image may be used to register the attenuation image to PET (e.g., to avoid the registration being influenced by any artefacts in the PET image due to attenuation mismatch), it should be appreciated that the method 800 of FIG. 8 may correct the first attenuation-corrected PET image. In another embodiment, method 800 may be used with a non-attenuation corrected PET image as well. However, for this to generate reliable results, additional blocks may be required. For instance, the derivations may further require accounting for errors in the scatter estimate. Thus, a separate scatter correction step may therefore be provided.

It should be appreciated that due to observations described above with reference to the local nature of the image-based correction, it may be sufficient to perform the registration only in a neighborhood of the region of interest. For example, in the context of tumor imaging with PET/CT, it may be sufficient to find misalignment between the tumor in the CT and PET images. As a result, a local registration process may be performed quickly by estimating the center of the tumor on both images.

Figure 9:
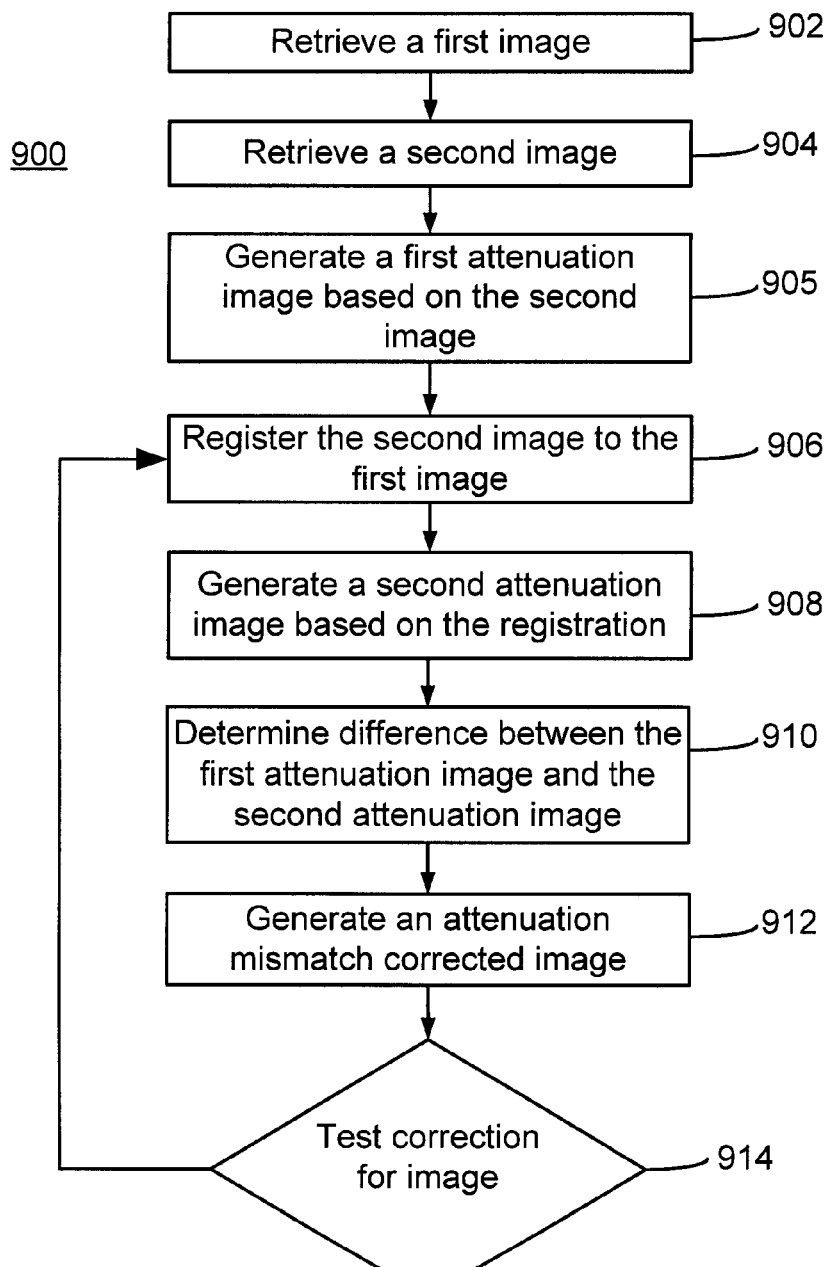
FIG. 9 depicts a flow chart showing a method of providing image-based correction according to an exemplary embodiment of the disclosure.

FIG. 9 depicts a flow chart showing a method of providing image-based correction 900 according to an exemplary embodiment of the disclosure. The exemplary method 900 is provided by way of example, as there are a variety of ways to carry out methods disclosed herein. The method 900 shown in FIG. 9 may be executed or otherwise performed by one or a combination of various systems. The method 900 is described below as carried out by the system 100 shown in FIG. 1 by way of example, and various elements of the system 100 are referenced in explaining the example method of FIG. 9. Each block shown in FIG. 9 represents one or more processes, methods, or subroutines carried in the exemplary method 900. A computer readable media comprising code to perform the acts of the method 900 may also be provided. In this example, which is similar to method 800 of FIG. 8, an attenuation mismatch estimate may be obtained; however, an additional step for correcting the image may be provided. Referring to FIG. 9, the exemplary method 900 may begin at block 902.

At block 902, a first image may be retrieved. The first image may be an attenuation corrected PET or SPECT image that may have been wrongly corrected (e.g., contains artifacts). At block 904, a second image may be retrieved. The second image may be an image used for attenuation correction, such as CT image, an MRI, or other similar image used for attenuation correction. At block 905, a first attenuation image based on the second image may be generated. At block 906, the second image may be registered to the first. At block 908, a second attenuation image may be generated based on the second image. At block 910, the difference between the first attenuation image and the second attenuation image may be determined. At block 912, an attenuation mismatch corrected image may be generated. Similar to FIG. 6, at block 914, the method 900 may also test the correction for the attenuation mismatch corrected image. For example, a test to check whether the correction is larger than a predetermined threshold may be provided. If so, the method 900 may repeat blocks 906, 908, and 910 to generate an attenuation mismatch corrected image. In this case, block 906 the second image may be registered to the new emission image obtained in the previous iteration. Other various embodiments may also be provided.

Figure 10:
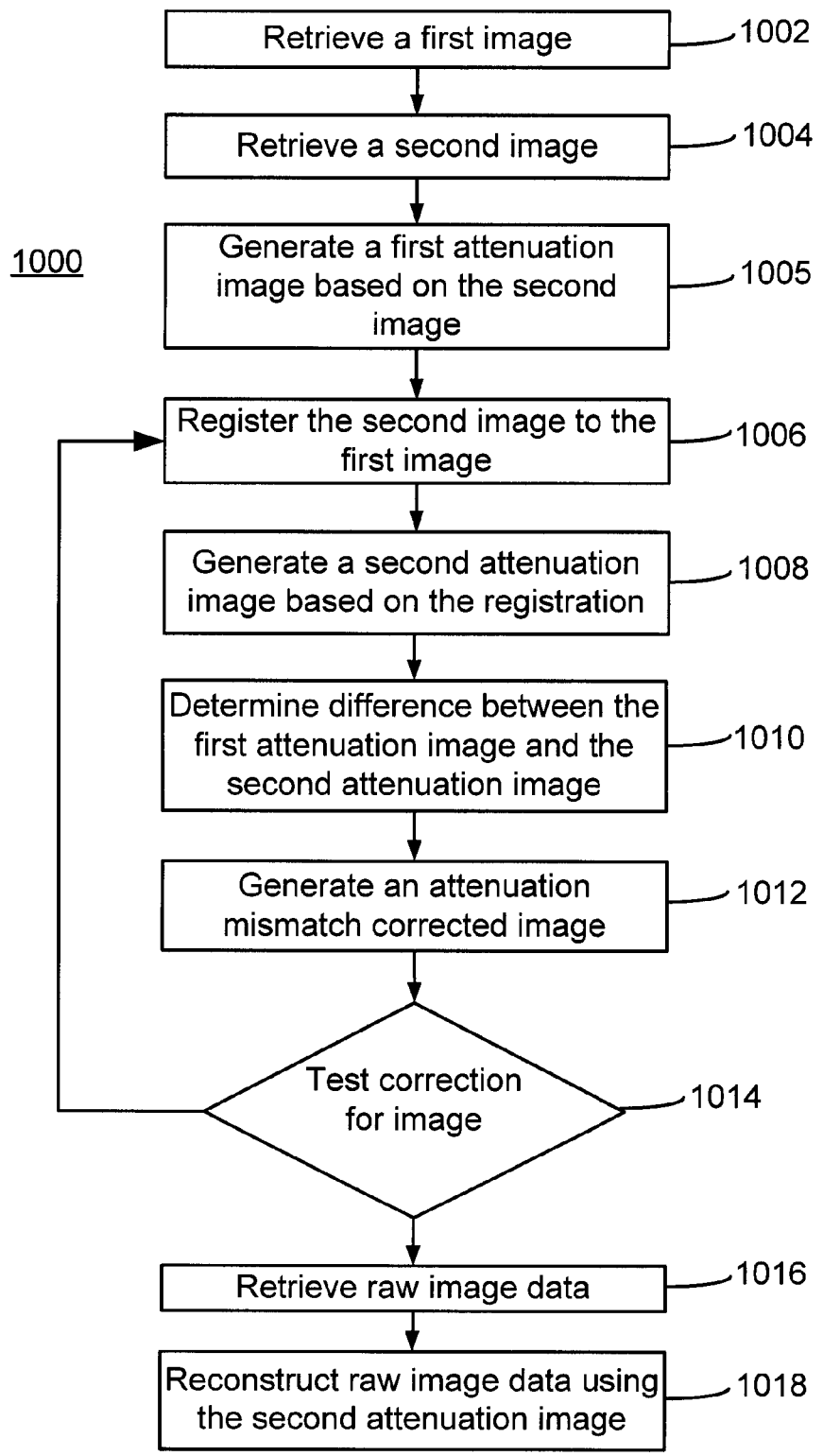
FIG. 10 depicts a flow chart showing a method of providing image-based correction according to an exemplary embodiment of the disclosure.

It should be appreciated that raw emission data may not be required since attenuation mismatch correction data may be provided from the images (e.g., CT or PET images, etc.). However, raw emission data may still be used for fine tuning or reconstructing PET images in the event such data may be available. For example, FIG. 10 depicts a flow chart showing a method of providing image-based correction 1000 according to an exemplary embodiment of the disclosure. Specifically, the method 1000 may obtain a more accurate registration of an attenuation mismatched corrected image.

The exemplary method 1000 is provided by way of example, as there are a variety of ways to carry out methods disclosed herein. The method 1000 shown in FIG. 10 may be executed or otherwise performed by one or a combination of various systems. The method 1000 is described below as carried out by the system 100 shown in FIG. 1 by way of example, and various elements of the system 100 are referenced in explaining the example method of FIG. 10. Each block shown in Figure 1000 represents one or more processes, methods, or subroutines carried in the exemplary method 1000. A computer readable media comprising code to perform the acts of the method 1000 may also be provided. Referring to Figure 1000, the exemplary method 1000 may begin at block 1002.

At block 1002, a first image may be retrieved. The first image may be an attenuation corrected PET or SPECT image that may have been wrongly corrected (e.g., contains artifacts). At block 1004, a second image may be retrieved. The second image may be an image used for attenuation correction, such as CT image, an MRI, or other similar image used for attenuation correction. At block 1005, a first attenuation image based on the second image may be generated. At block 1006, the second image may be registered to the first. At block 1008, a second attenuation image may be generated based on the second image. At block 1010, the different between the first attenuation image and the second attenuation image may be determined. At block 1012, an attenuation mismatch corrected image may be generated. Similar to FIG. 9, at block 914, the method 1000 may also test the correction for the attenuation mismatch corrected image. For example, a test to check whether the correction is larger than a predetermined threshold may be provided. If so, the method 1000 may repeat blocks 1006, 1008, and 1010 to generate an attenuation mismatch corrected image (e.g., potentially using the attenuation mismatch corrected image in block 1006, as noted in FIG. 9).

In addition, at block 1016, raw image data may also be retrieved. In this example, raw image data may be stored at various locations, such as a scanner system, one or more data storage systems (local or remote to the scanning system), or other similar storage systems. At block 1018, reconstruction of the raw image data may be provided based on the second attenuation image at from block 1008. Other various embodiments may also be provided.

It should be appreciated that since reconstruction at block 1018 may be an iterative reconstruction, additional steps may also be incorporated. For example, block 1018 may use the first image of block 1002 or the attenuation mismatch corrected image of Figure 1012 as a starting point for reconstruction the raw image data. Other variations may also be provided.

Other methods may be used to find a better attenuation image depending on the cause for the mismatch. In another embodiment, in the event the PET/SPECT data is ungated, and the CT is acquired fast, and hence essentially frozen in motion, and the CT was used for the attenuation correction of the emission image, embodiments of the present disclosure may estimate a more appropriate attenuation image by blurring the CT image, potentially using a model for the motion using as input extra measurements (e.g., as provided by the Varian™ RPM™ system). The required blurring may further be estimated so that the structure(s) of interest (e.g. myocardium) may be aligned with the PET image. The blurred CT obtained by this method may then be used to find a new CTAC image $\mu^{new}$ which may, in turn, be used to find an appropriate correction for the emission image. Similar to the registration process, this process may be repeatable.

Embodiments of the present disclosure may also be applied in cases where the attenuation mismatch is not due to motion. In one embodiment, the CT image used for the CTAC may have streak-like artifacts due to metal implants. A post-processed image may be used to estimate $\mu^{new}$ and the above formulas may also be used to computed a correction term for the emission image. In another application, CT Hounsfield units may appear similar for bone and some iodine-based contrast agents, while the PET attenuation factors may be different. The similarity between the Hounsfield units in the CT image may result in an error in the CTAC and hence an attenuation mismatch. In one embodiment, this mismatch may be corrected by differentiating between bone and other tissue and computing the attenuation mismatch factors.

Although embodiments of the present disclosure are directed primarily to automated embodiments, it should be appreciated that semi-automatic techniques may also be provided. For example, image-based attenuation mismatch correction may also be performed by a clinician or other similar party at a local or remote workstation to review the correction data. In this example, the clinician or other similar party may provide additional input, data, and/or feedback to assist with registration and other correction steps. As a result, greater flexibility and reliability may be provided.

It should also be appreciated that while embodiments of the present disclosure are primarily described with respect to PET and/or SPECT images, image-based attenuation correction images may also be provided for other systems and embodiments. However, it should be appreciated that approximations and formulas may be varied and/or tailored for providing image-based corrections these other implementations.

While the foregoing specification illustrates and describes the preferred embodiments of this disclosure, it is to be understood that the disclosure is not limited to the precise construction disclosed herein. The disclosure may be embodied in other specific forms without departing from the spirit or essential attributes. Accordingly, reference should be made to the following claims, rather than to the foregoing specification, as indicating the scope of the disclosure.

What is claimed is:

1. A method for providing image-based correction, the method comprising:
   retrieving a first image;
   retrieving a second image;
   generating a first attenuation image based on the second image;
   registering the second image to the first image;
   generating a second attenuation image based on the registration; and
   providing an attenuation mismatch estimate based on the first attenuation image and the second attenuation image.

2. The method of claim 1, wherein the first image is a non-attenuation corrected PET image or a non-attenuation corrected SPECT image.

3. The method of claim 1, wherein the second image is an image used for attenuation correction.

4. The method of claim 3, wherein the image used for attenuation correction is a CT image, an MRI image, a PET image, or a SPECT image.

5. The method of claim 1, wherein the first image and the second image are acquired from one or more data storage systems.

6. The method of claim 5, wherein providing an attenuation mismatch estimate comprises determining the difference between the first attenuation image and the second attenuation image.

7. The method of claim 1, wherein the second image is registered locally to the first image.

8. The method of claim 1, further comprising generating an attenuation mismatch corrected image based on the attenuation mismatch estimate.

9. The method of claim 8, further comprising testing the attenuation mismatch corrected image to determine whether the correction is larger than a predetermined threshold.

10. The method of claim 9, wherein the predetermined threshold comprises at least one of time, accuracy, and customized setting.

11. The method of claim 1, further comprising:
    retrieving raw image data; and
    reconstructing the raw image data to provide an improved correction image.

12. The method of claim 11, wherein the raw image data is retrieved from at least one of a data storage system and a scanner.

13. The method of claim 12, wherein reconstructing the raw image data uses the second attenuation image.

14. A computer readable media comprising code to perform the acts of the method of claim 1.

15. A system for providing for image-based correction, the system comprising:
    at least one receiver to retrieve a first image and a second image from one or more data storage systems; and
    one or more processors to generate a first attenuation image based on the second image, register the second image to the first image, generate a second attenuation image based on the registration, and provide an attenuation mismatch estimate for image-based correction based on the first attenuation image and the second attenuation image.

* * * * *